(12) United States Patent
Jensen

(10) Patent No.: US 8,838,331 B2
(45) Date of Patent: Sep. 16, 2014

(54) PAYLOAD MATERIAL DENSITY CALCULATION AND MACHINE USING SAME

(71) Applicant: Caterpillar Inc., Peoria, IL (US)

(72) Inventor: Jeffrey Edward Jensen, Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 172 days.

(21) Appl. No.: 13/624,111

(22) Filed: Sep. 21, 2012

(65) Prior Publication Data

US 2014/0088822 A1    Mar. 27, 2014

(51) Int. Cl.
*G01M 17/00* (2006.01)
*G06F 7/00* (2006.01)
*G06F 19/00* (2011.01)

(52) U.S. Cl.
USPC ............................................ 701/34.4; 702/23

(58) Field of Classification Search
USPC ......... 701/34.4, 48, 50, 99, 2, 25, 29.6, 70, 3, 701/33.6, 33.7, 29.2, 32.9, 29.1, 14, 8, 13, 701/32.6, 104, 472, 1; 702/23, 50, 25, 188, 702/173, 174, 21, 19, 34, 85, 75, 175, 138, 702/122, 66; 239/1; 180/167
See application file for complete search history.

(56) References Cited

U.S. PATENT DOCUMENTS

| | | | |
|---|---|---|---|
| 4,614,477 A | 9/1986 | Hagenbuch | |
| 4,995,468 A * | 2/1991 | Fukuda | 177/139 |
| 5,105,896 A * | 4/1992 | Kyrtsos | 177/139 |
| 5,220,968 A | 6/1993 | Weber | |
| 5,929,389 A * | 7/1999 | Keuper | 177/141 |
| 6,505,106 B1 * | 1/2003 | Lawrence et al. | 701/29.3 |
| 6,518,519 B1 * | 2/2003 | Crane et al. | 177/136 |
| 6,931,772 B2 | 8/2005 | Furuno et al. | |
| 7,795,547 B2 * | 9/2010 | Hansen | 177/1 |
| 7,912,612 B2 * | 3/2011 | Janardhan et al. | 701/50 |
| 8,024,095 B2 * | 9/2011 | Mintah et al. | 701/50 |
| 8,156,048 B2 * | 4/2012 | Mintah et al. | 705/50 |
| 8,428,832 B2 * | 4/2013 | Marathe et al. | 701/50 |
| 8,515,627 B2 * | 8/2013 | Marathe et al. | 701/50 |
| 8,660,758 B2 * | 2/2014 | Janardhan et al. | 701/50 |
| 2005/0085963 A1 * | 4/2005 | Kapolka et al. | 701/29 |
| 2008/0005938 A1 | 1/2008 | Aebischer et al. | |
| 2009/0125180 A1 * | 5/2009 | Berkobin et al. | 701/35 |
| 2009/0192674 A1 * | 7/2009 | Simons | 701/37 |
| 2011/0066336 A1 | 3/2011 | Adolfson | |

(Continued)

*Primary Examiner* — Thomas G Black
*Assistant Examiner* — Robert Payne
(74) *Attorney, Agent, or Firm* — Baker Hostetler

(57) ABSTRACT

A method of determining payload material density includes a step of determining a capacity volume of a work tool of a machine using an electronic controller of the machine. The work tool is loaded with an initial amount of loaded material matching the capacity volume, and an onboard payload mass calculation algorithm is executed using the electronic controller to determine a mass of the initial amount of loaded material. A density of the initial amount of loaded material is calculated responsive to the mass of the initial amount of loaded material and the capacity volume using the electronic controller. The density of the initial amount of loaded material is stored using the electronic controller, and a productivity datum is calculated responsive to the density of the initial amount of loaded material and a subsequent amount of loaded material.

20 Claims, 3 Drawing Sheets

(56) References Cited

U.S. PATENT DOCUMENTS

| | | | |
|---|---|---|---|
| 2011/0087400 A1* | 4/2011 | Lorimier | 701/35 |
| 2012/0179360 A1* | 7/2012 | Montelimard | 701/123 |
| 2013/0024088 A1* | 1/2013 | Suzuki et al. | 701/102 |
| 2013/0035810 A1* | 2/2013 | Spinelli | 701/17 |
| 2013/0046431 A1* | 2/2013 | Becker et al. | 701/25 |
| 2013/0073120 A1* | 3/2013 | Bailey et al. | 701/2 |
| 2013/0240722 A1* | 9/2013 | Coon et al. | 250/282 |
| 2014/0032130 A1* | 1/2014 | Berkobin et al. | 702/24 |

* cited by examiner

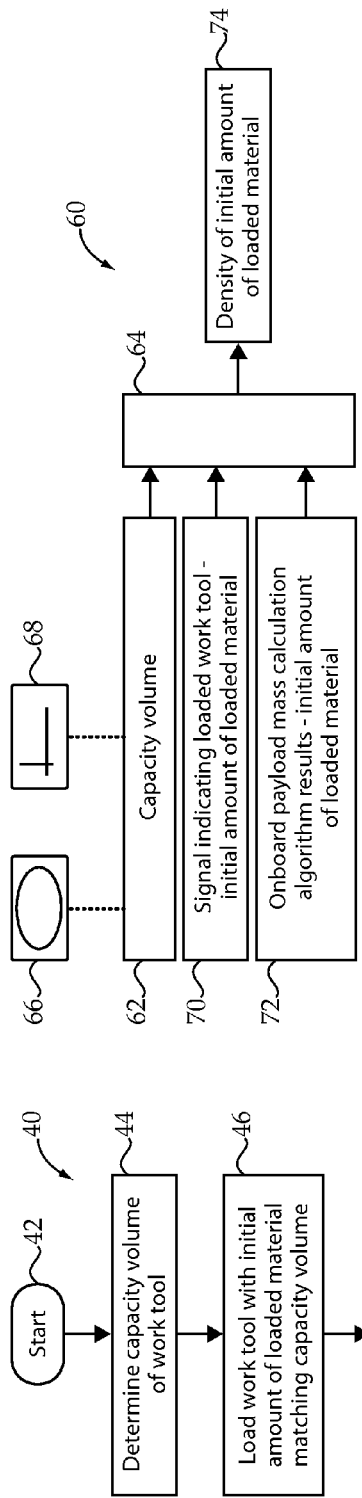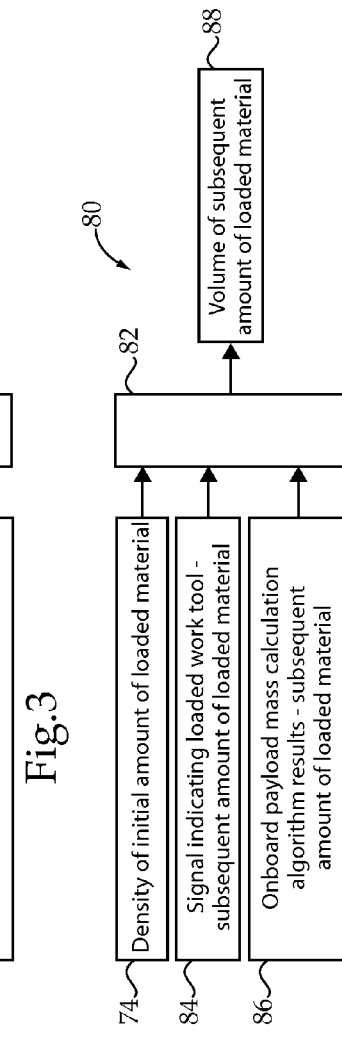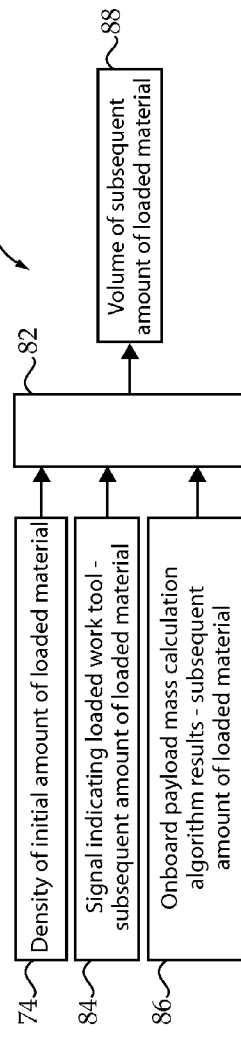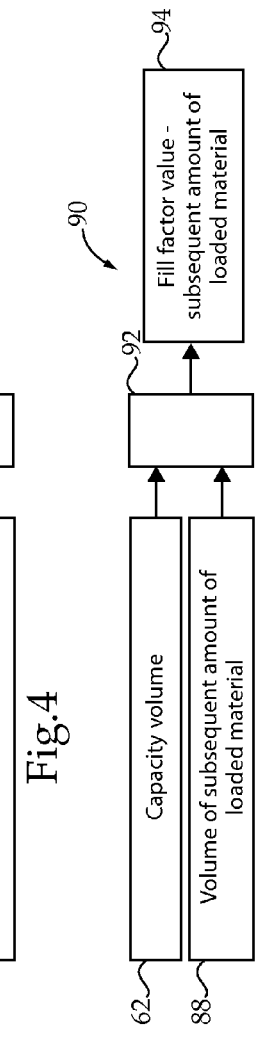

PAYLOAD MATERIAL DENSITY CALCULATION AND MACHINE USING SAME

TECHNICAL FIELD

The present disclosure relates generally to a method of determining density of payload material, and more particularly to determining payload material density based on a capacity volume of a machine work tool and an onboard payload mass calculation of an amount of loaded material matching the capacity volume.

BACKGROUND

Off-highway machines, such as, for example, loaders, are typically used to transport a payload material, such as, for example, rock, sand, dirt, or gravel, from one location to another. According to a particular work cycle, the loader may use a work tool, such as a bucket, to capture a portion of the payload material and transfer the captured portion of material to another location. Alternatively, a work cycle may include use of the loader to fill a larger payload capacity machine, such as a haulage truck, which is used to transport the material. According to these work cycles and others, it may be desirable to calculate the weight, or mass, of the payload material that is moved within or transported from a work site. This payload weight or mass calculation may be used to evaluate efficiency, productivity, and profitability of the work site operations.

A variety of onboard payload weight measurement systems exist for calculating or measuring the weight or mass of payload material in a loaded work tool. For example, one system, as disclosed in U.S. Pat. No. 4,635,739 to Foley et. al., uses strut pressure as an indication of payload mass. In particular, the disclosed system includes an electronic controller that monitors strut pressures, compensates for various inaccuracies introduced by load distribution and vehicle attitude, and correlates this information into an actual payload mass. As should be appreciated, this payload information allows the machine to be operated efficiently near a desired capacity without causing undue wear of machine components.

U.S. Patent Application Publication No. 2008/0005938 to Aebischer et al. discloses an apparatus for determining the load of an excavator bucket. In particular, the Aebischer et al. reference teaches the use of a distance-measuring camera supported by a boom of the excavator for measuring distances from the camera to at least three points on the excavator bucket. These measured distances, including a distance to the surface of the load, are used to determine a volume of the bucket load. Although volume information may also be useful in evaluating performance and productivity at a work site, the use of additional equipment, including a distance-measuring camera, may be undesirable.

The present disclosure is directed to one or more of the problems or issues set forth above.

SUMMARY OF THE DISCLOSURE

In one aspect, a method of determining payload material density includes a step of determining a capacity volume of a work tool of a machine using an electronic controller of the machine. The work tool is loaded with an initial amount of loaded material matching the capacity volume, and an onboard payload mass calculation algorithm is executed using the electronic controller to determine a mass of the initial amount of loaded material. A density of the initial amount of loaded material is calculated responsive to the mass of the initial amount of loaded material and the capacity volume using the electronic controller. The density of the initial amount of loaded material is stored using the electronic controller, and a productivity datum is calculated responsive to the density of the initial amount of loaded material and a subsequent amount of loaded material.

In another aspect, a machine includes a machine body supported by a conveyance. An operator interface is positioned within an operator control station, which is supported on the machine body. A work tool is pivotably attached to the machine body. An electronic controller is in communication with the operator interface and is configured to determine a capacity volume of the work tool. The electronic controller is also configured to receive a signal indicating the work tool is loaded with an initial amount of loaded material matching the capacity volume, and execute an onboard payload mass calculation algorithm to determine a mass of the initial amount of loaded material. The electronic controller is further configured to calculate a density of the initial amount of loaded material responsive to the mass of the initial amount of loaded material and the capacity volume, and store the density of the initial amount of loaded material. The electronic controller is also configured to calculate a productivity datum responsive to the density of the initial amount of loaded material and a subsequent amount of loaded material.

In another aspect, a non-transitory computer usable storage medium having computer readable program code thereon for determining payload material density includes computer readable program code for identifying a capacity volume of a work tool. The non-transitory computer usable storage medium also includes computer readable program code for receiving a signal indicating that the work tool is loaded with an initial amount of loaded material matching the capacity volume, and executing an onboard payload mass calculation algorithm to determine a mass of the initial amount of loaded material responsive to the signal. The non-transitory computer usable storage medium also includes computer readable program code for calculating a density of the initial amount of loaded material responsive to the mass of the initial amount of loaded material and the capacity volume, and storing the density of the initial amount of loaded material. Computer readable program code is also provided for calculating a productivity datum responsive to the density of the initial amount of loaded material and a subsequent amount of loaded material.

BRIEF DESCRIPTION OF THE DRAWINGS

FIG. 2 is a logic flow diagram of a method of determining payload material density onboard the machine of FIG. 1, according to one aspect of the present disclosure;

FIG. 3 is exemplary control logic corresponding to a payload material density algorithm, according to another aspect of the present disclosure;

FIG. 4 is exemplary control logic corresponding to a productivity datum calculation algorithm, according to another aspect of the present disclosure;

FIG. 5 is exemplary control logic corresponding to another productivity datum calculation algorithm, according to another aspect of the present disclosure.

DETAILED DESCRIPTION

Figure 1:
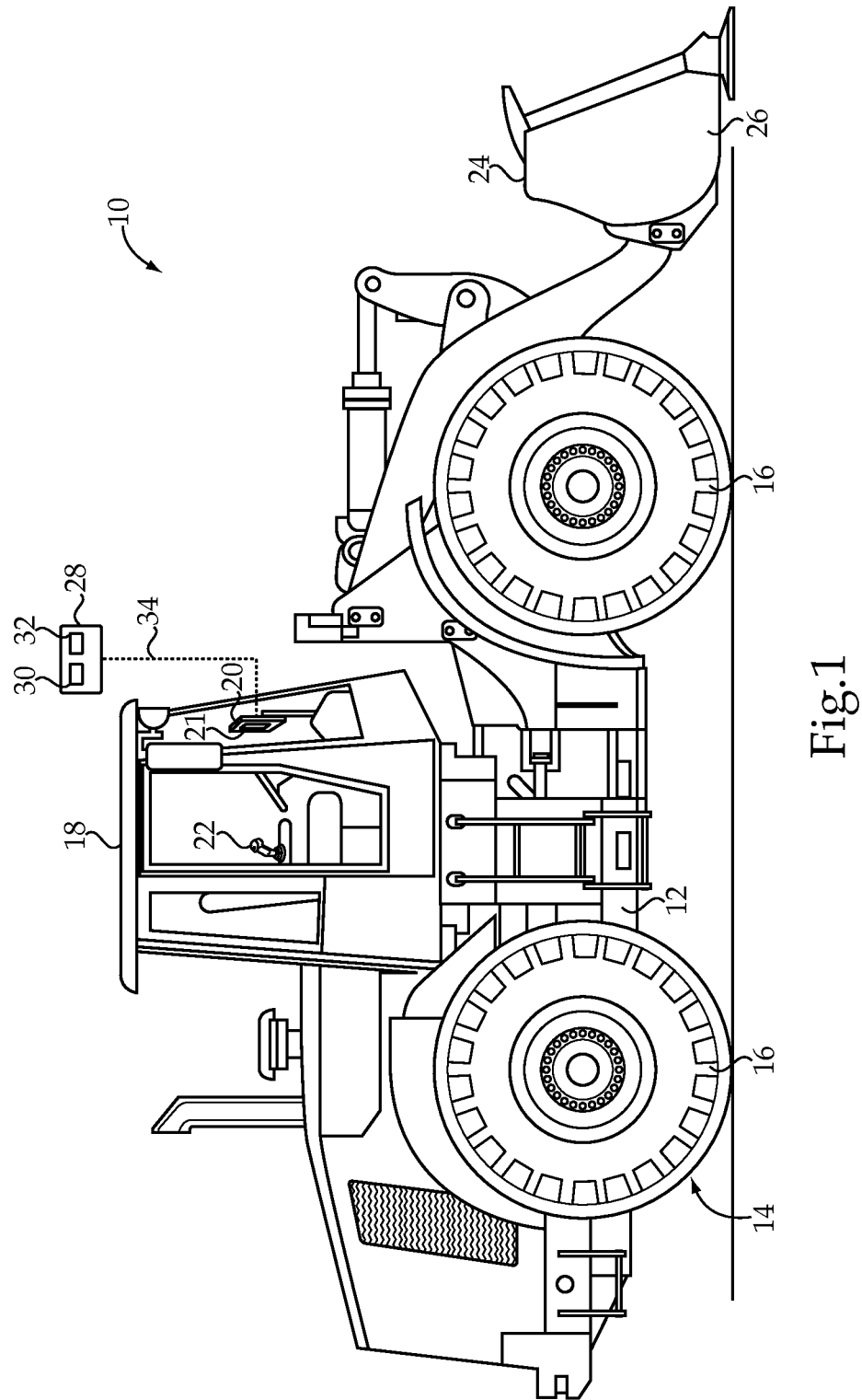
FIG. 1 is a side diagrammatic view of a machine, according to the present disclosure.

An exemplary embodiment of a machine 10 is shown generally in FIG. 1. The machine 10 may be an off-highway machine, such as, for example, a wheel loader, or any other machine capable of performing work operations as described herein. The machine 10 generally includes a machine body, or frame, 12 supported by a conveyance 14, which may include wheels 16 (as shown) or alternative ground-engaging propulsion elements. The machine 10 also includes an operator control station 18 supported on the machine body 12 and housing an operator interface 20, including an operator display 21, for displaying various operational information relating to the machine 10 and facilitating operator input of various control information. Additional controls and devices may also be positioned within the operator control station 18, including, for example, one or more controllers 22 for controlling a work tool, or implement, 24, such as a bucket 26 (as shown).

The machine 10 also includes at least one electronic controller 28, which may be part of a machine control system, for controlling, coordinating, and evaluating various operations of the machine 10. The electronic controller 28 may be of standard design and may include a processor 30, such as, for example, a central processing unit, a memory 32, and an input/output circuit 34 that facilitates communication internal and external to the electronic controller 28. The processor 30, for example, may control operation of the electronic controller 28 by executing operating instructions, such as, for example, computer readable program code stored in the memory 32, wherein operations may be initiated internally or externally to the electronic controller 28. Control schemes may be utilized that monitor outputs of systems or devices, such as, for example, sensors, actuators, or control units, via the input/output circuit to control inputs to various other systems or devices. The memory 32, as used herein, may comprise temporary storage areas, such as, for example, cache, virtual memory, or random access memory, or permanent storage areas, such as, for example, read-only memory, removable drives, network/internet storage, hard drives, flash memory, memory sticks, or any other known volatile or non-volatile data storage devices. One skilled in the art will appreciate that any computer based system or device utilizing similar components for controlling the machine systems or components described herein, is suitable for use with the present disclosure.

The electronic controller 28 may communicate with various systems and components of the machine 10 via one or more wired and/or wireless communications lines, such as the input/output circuit 34. For example, the electronic controller 28 may communicate with the operator interface 28 for receiving operator input and displaying operational information to the operator, as will be described below. Although only one electronic controller 28 is described herein, it should be appreciated that an electronic control system for the machine 10 may include numerous electronic controllers for controlling various systems and components of the machine 10 in a known manner. For example, electronic controller 28, or an alternative electronic controller, may control movement of the work tool 24 based on operator manipulation of the controller 22.

Turning now to FIG. 2, there is shown a logic flow diagram 40 representing an exemplary method of determining payload material density onboard the machine 10, according to the present disclosure. The method may be implemented by the electronic controller 28, or other similar control device, of the machine 10. According to one example, the steps implementing the disclosed method, or a portion thereof, may be in the form of computer readable program code stored in the memory 32 of the electronic controller 28 and executed by the processor 30 of the electronic controller 28, or other computer usable medium. The method may run continuously or may be initiated in response to one or more predetermined events, such as an operator request, as described below.

The method begins at a START, Box 42. From Box 42, the method proceeds to Box 44, which includes the step of determining a capacity volume of the work tool 24. The capacity volume, which may represent a measure of the volume of payload material the work tool 24 can support when the work tool 24 is fully occupied with material, may be determined in a number of ways, as will be discussed with reference to FIG. 3 below. Ultimately, the capacity volume will be received at and used by the electronic controller 28. The method also includes a step of loading the work tool 24 with an initial amount of loaded material matching the capacity volume, at Box 46. For example, an operator may load the work tool 24 in a known manner such that the initial amount of loaded material corresponds, as closely as possible, to the capacity volume. As should be appreciated by those skilled in the art, this method step may include the operator attempting to load the work tool 24 to a fill factor of 100%. Particular operations to achieve the 100% fill factor will be discussed in greater detail below.

After the work tool 24 is loaded to match the capacity volume, an onboard payload mass calculation algorithm is executed, such as by the electronic controller 28 or an alternative controller, to determine a mass, or weight, of the initial amount of loaded material, at Box 48. For example, the operator may indicate a fully loaded condition of the work tool 24 using the operator interface 20 and, as a result, the onboard payload mass calculation algorithm may be initiated. A variety of onboard payload mass calculation algorithms are known and, as such, will not be discussed herein in further detail. However, for exemplary purposes only, an onboard payload mass calculation algorithm may utilize measurements of strut pressures or cylinder pressures to arrive at a mass calculation. This mass calculation is ultimately received at the electronic controller 28 and used in the calculation described below.

At Box 50, a density of the initial amount of loaded material may be calculated based on the calculated mass of the initial amount of loaded material (Box 48), and the capacity volume of the work tool 24 (Box 44). For example, substituting the mass and volume values determined above into the equation $d=m/v$, where $d$=density, $m$=mass, and $v$=volume, will yield an estimate of the density of the initial amount of loaded material. The density value is stored by the electronic controller 28, at Box 52, and used to calculate a productivity datum, at Box 54. For example, and as will be described in greater detail below, a productivity datum may be calculated responsive to the density of the initial amount of loaded material and a subsequent amount of loaded material. The method then proceeds to an END, at Box 56.

According to specific implementations of the method of FIG. 2, the electronic controller 28 may be configured to determine a density of an initial amount of loaded material and later utilize the density calculation to arrive at various productivity data. In particular, as shown in FIG. 3, the electronic controller 28 may include a payload material density algorithm 60 for calculating a density of an initial amount of loaded material. As shown, a capacity volume 62 of the work tool 24 may be received as an input to a controller 64, such as the electronic controller 28. For example, the capacity volume 62 may be directly input by an operator using an operator interface device 66, such as the operator interface 20 of FIG. 1, or may be selected from a work tool volume map 68, which may be stored in the memory 32. The work tool volume map 68 may, for example, be provided by the machine manufacturer and may include capacity volumes of various work tools compatible with the machine 10.

The controller 64 may also receive a signal 70, or other indication, indicative of a loaded work tool. In particular, the controller 64 may be provided with an indication that the work tool 24 is loaded with an initial amount of loaded material matching the capacity volume 62 of the work tool 24. According to one example, the signal 70 may be responsive to the initiation by an operator of an onboard payload mass calculation algorithm. For example, the user may be prompted to load the work tool 24 toward a 100% fill factor. After the operator is satisfied that the work tool 24 is loaded, as closely as possible, to match the capacity volume 62, the operator may initiate the onboard payload mass calculation algorithm to arrive at a mass 72 of the initial amount of loaded material. The mass 72, along with the capacity volume 62, is then used by the controller 64 to arrive at the density 74 of the initial amount of loaded material, as described above.

The density 74 may be stored, such as in the memory 32, and later used by the electronic controller 28 to calculate productivity data. For example, as shown in FIG. 4, the electronic controller 28 may include a first productivity datum calculation algorithm 80. The productivity datum calculation algorithm 80 may include a controller 82, such as the electronic controller 28, receiving as inputs the density 74, calculated as described in FIG. 3, and a signal 84 indicative of a subsequent loading of the work tool 24. According to a subsequent loading of the work tool 24 with a subsequent amount of loaded material, it is not necessary that the operator attempt to load the work tool 24 with an amount of material matching the capacity volume. For example, after the density calculation is completed, the operator may load the work tool 24 according to operating requirements pertaining to the particular work cycle.

After the work tool 24 has been loaded with a subsequent amount of loaded material, the controller 82 may initiate operation of the onboard payload mass calculation algorithm. For example, the operator may initiate execution of the onboard payload mass calculation algorithm using the operator interface 20 after the work tool 24 has been loaded with the subsequent amount of loaded material. The onboard payload mass calculation algorithm may measure or calculate a mass 86 of the subsequent amount of loaded material in a known manner. Utilizing the mass 86 of the subsequent amount of loaded material and the previous density 74, calculated with respect to the initial amount of loaded material, the controller 82 may calculate, or estimate, a volume 88 of the subsequent amount of loaded material. For example, substituting the mass 86 and density 74 values into the equation d=m/v, where d=density, m=mass, and v=volume, will yield a volume calculation or estimation 88 for the subsequent amount of loaded material. It should be appreciated that useful productivity data may represent an evaluation of work performed over time or during a number of work cycles and, thus, the volume and/or mass calculations may ultimately be calculated by the electronic controller 28 as volume and/or mass per unit time or per number of work cycles.

The electronic controller 28 may also include a second productivity datum calculation algorithm 90, as shown in FIG. 5. The productivity datum calculation algorithm 90 may also include a controller 92, such as the electronic controller 28, receiving as inputs the capacity volume 62, as described in FIG. 3, and the volume 88 of the subsequent amount of loaded material, as calculated above. Utilizing the capacity volume 62 and the estimated volume 88, the controller 92 may estimate a fill factor value 94 for the subsequent amount of loaded material. For example, the fill factor value 94 may represent a percentage, or portion, of the capacity volume 62, with the capacity volume 62 representing a 100% fill factor. Further, the fill factor value 94 may be evaluated over time by the electronic controller 28 to arrive at a fill factor average per unit time or per number of work cycles. The fill factor value 94, along with the estimated volume 88, density 74, or any combination thereof, may be displayed on the operator display 21, stored in the memory 32, and/or transmitted offboard the machine 10 for evaluation.

Figure 6:
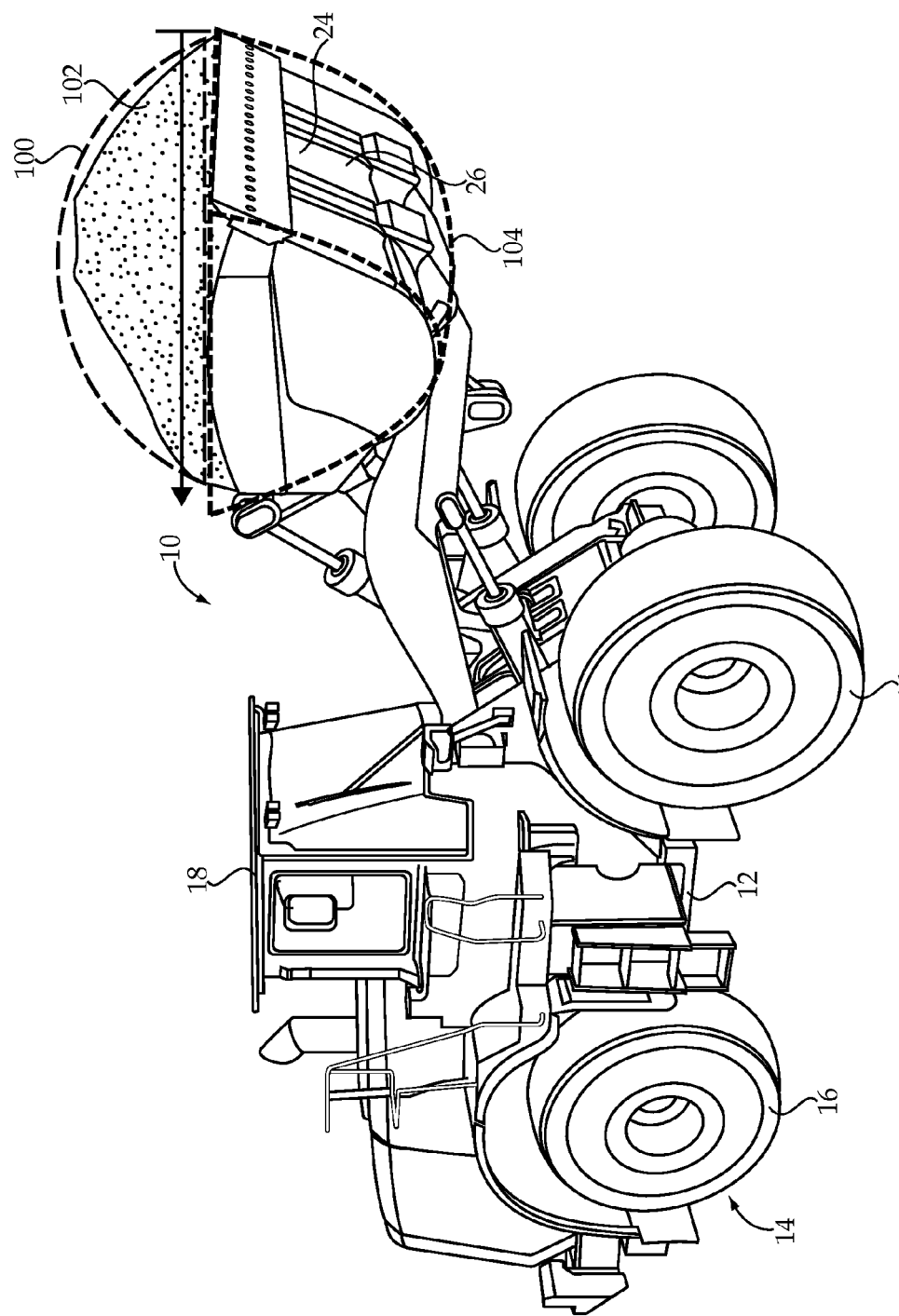
FIG. 6 is a perspective view of the machine of FIG. 1, depicting a work tool of the machine supporting payload material.

It should be appreciated that the accuracy of the density 74, calculated as described herein, and the later calculated volume 88 and fill factor value 94 relies on the skill of the operator in loading the work tool 24 with an initial amount of loaded material matching the capacity volume 62. To achieve the approximate 100% fill factor, the operator may employ any of a number of different loading techniques and/or may utilize additional machines, tools, or objects, as necessary. For example, as shown in FIG. 6, the operator may initially load the work tool 24 with an excess amount 100 of loaded material 102 according to a normal loading operation. To match the capacity volume 104 of the work tool 24, the excess amount 100 of loaded material 102 may be removed, such as by rapidly moving the work tool 24 from side to side, or by scraping a top surface of the work tool 24 along an accessible surface or edge, such as an overhanging edge of a haulage truck. It should be appreciated that alternative means for approximating the 100% fill factor, including manually loading and/or removing material, along with other known means, are also contemplated and are within the scope of the present disclosure.

INDUSTRIAL APPLICABILITY

The present disclosure is generally applicable to any machine having a work tool configured to support a payload material. Further, the present disclosure finds particular applicability to machines, such as, for example, loaders, having onboard payload mass calculation algorithms executable thereon. The present disclosure also finds general applicability to strategies for providing useful productivity data in work site environments.

Referring generally to FIGS. 1-6, a machine 10, such as a loader, may include a machine body 12 supported by a conveyance 14. The machine 10 also includes an operator control station 18 supported on the machine body 12 and housing an operator interface 20, including an operator display 21. A work tool 24 is also supported on the machine body 12 and is configured to support payload material. For example, the machine 10 may use the work tool 24 to transport the payload material or load a larger payload capacity machine, such as a haulage truck. During operation, it may be desirable to calculate the weight, or mass, of the payload material that is captured and moved by the machine 10, such as by using a known onboard payload mass calculation algorithm.

According to the present disclosure, the payload material density may also be calculated onboard the machine 10, and may be used to estimate other productivity data, including the volume and fill factor of subsequent loads of payload material. In particular, as shown in FIG. 3, an electronic controller 28 of the machine 10 may include a payload material density algorithm 60 for calculating a density of an initial amount of loaded material. According to the payload material density algorithm 60, a capacity volume 62 of the work tool 24 may be received as an input to a controller 64, which may represent the electronic controller 28. The controller 64 may also receive a signal 70, or other notification, indicating the work tool 24 has been loaded with an initial amount of loaded material matching the capacity volume 62 of the work tool 24. After the work tool 24 has been loaded, as closely as possible, to a 100% fill factor, an onboard payload mass calculation algorithm is executed to calculate a mass 72 of the initial amount of loaded material. The mass 72 and the capacity volume 62 are then used by the controller 64 to arrive at the density 74 of the initial amount of loaded material.

The density 74 may be useful in determining the type of material being moved, and the moisture content of the material being moved. As should be appreciated, the density 74 that is calculated may change for different materials, or different mixtures of materials, and may also change for the same material over time. Thus, it may be useful to perform the density calculation described herein at different times throughout a work shift and/or as it becomes evident that different materials are being loaded with the work tool 24. The density 74 may be stored and, perhaps, routinely updated, in the memory 32, and used by the electronic controller 28 to calculate various useful data, including productivity data.

For example, as shown in FIG. 4, the electronic controller 28 may include a first productivity datum calculation algorithm 80. The productivity datum calculation algorithm 80 may include a controller 82, such as the electronic controller 28, receiving as inputs the density 74 of the initial amount of loaded material and a signal 84 indicative of a subsequent loading of the work tool 24. The onboard payload mass calculation algorithm may be initiated after the work tool 24 has been loaded to calculate or measure a mass 86 of the subsequent amount of loaded material in a known manner. Utilizing the mass 86 of the subsequent amount of loaded material and the previous density 74, calculated with respect to the initial amount of loaded material, the controller 82 may calculate, or estimate, a volume 88 of the subsequent amount of loaded material.

The electronic controller 28 may also include a second productivity datum calculation algorithm 90, as shown in FIG. 5. The second productivity datum calculation algorithm 90 may also include a controller 92, such as the electronic controller 28, receiving as inputs the capacity volume 62 and the volume 88 of the subsequent amount of loaded material. Utilizing the capacity volume 62 and the estimated volume 88, the controller 92 may estimate a fill factor value 94 for the subsequent amount of loaded material. The fill factor value 94, along with the estimated volume 88, density 74, or any combination thereof, may be used to evaluate efficiency, productivity, and profitability of the work site operations.

The payload material density, and productivity data based on the payload material density, which may include mass and/or volume calculations per unit time and/or fill factor averages over time, may be calculated onboard a machine with minimal machine modifications. For example, many current machines, such as loaders, used to transport payload material are equipped with an onboard payload mass calculation system. The strategy provided herein uses the onboard mass calculation in addition to productivity data calculation algorithms to arrive at additional productivity data that may be displayed to the operator and/or used in later evaluations. As described herein, the strategy relies upon the skill of the operator to load a machine work tool toward the capacity volume and, thus, reduces the need for additional load measuring equipment.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A method of determining payload material density, including steps of:
   determining a capacity volume of a work tool of a machine using an electronic controller of the machine;
   loading the work tool with an initial amount of loaded material matching the capacity volume;
   executing an onboard payload mass calculation algorithm using the electronic controller to determine a mass of the initial amount of loaded material;
   calculating a density of the initial amount of loaded material responsive to the mass of the initial amount of loaded material and the capacity volume using the electronic controller;
   storing the density of the initial amount of loaded material using the electronic controller; and
   calculating a productivity datum responsive to the density of the initial amount of loaded material and a subsequent amount of loaded material.

2. The method of claim 1, wherein the step of determining the capacity volume includes receiving the capacity volume as an input from an operator interface.

3. The method of claim 1, wherein the step of determining the capacity volume includes selecting the capacity volume from a work tool volume map stored in a memory.

4. The method of claim 1, wherein the step of loading the work tool includes loading the work tool with an excess amount of loaded material, and removing the excess amount of loaded material.

5. The method of claim 1, further including:
   executing the onboard payload mass calculation algorithm using the electronic controller to determine a mass of the subsequent amount of loaded material; and
   calculating a volume of the subsequent amount of loaded material responsive to the mass of the subsequent amount of loaded material and the density of the initial amount of loaded material.

6. The method of claim 5, further including calculating a fill factor value of the subsequent amount of loaded material responsive to the volume of the subsequent amount of loaded material and the capacity volume.

7. The method of claim 1, further including displaying the productivity datum on an operator display.

8. A machine, comprising:
   a machine body supported by a conveyance;
   an operator interface positioned within an operator control station, wherein the operator control station is supported on the machine body;
   a work tool pivotably attached to the machine body; and
   an electronic controller in communication with the operator interface and configured to determine a capacity volume of the work tool, receive a signal indicating that the work tool is loaded with an initial amount of loaded material matching the capacity volume, execute an onboard payload mass calculation algorithm to determine a mass of the initial amount of loaded material, calculate a density of the initial amount of loaded material responsive to the mass of the initial amount of loaded material and the capacity volume, store the density of the initial amount of loaded material, and calculate a productivity datum responsive to the density of the initial amount of loaded material and a subsequent amount of loaded material.

9. The machine of claim 8, wherein the electronic controller receives the capacity volume as an input from the operator interface.

10. The machine of claim 8, further including a work tool volume map stored in a memory of the electronic controller, wherein the electronic controller selects the capacity volume from the work tool volume map.

11. The machine of claim 8, wherein the electronic controller is further configured to:
receive a second signal indicating that the work tool is loaded with a subsequent amount of loaded material;
execute the onboard payload mass calculation algorithm to determine a mass of the subsequent amount of loaded material; and
calculate a volume of the subsequent amount of loaded material responsive to the mass of the subsequent amount of loaded material and the density of the initial amount of loaded material.

12. The machine of claim 11, wherein the electronic controller is further configured to calculate a fill factor value of the subsequent amount of loaded material responsive to the volume of the subsequent amount of loaded material and the capacity volume.

13. The machine of claim 8, wherein the operator interface includes an operator display configured to display the productivity datum.

14. The machine of claim 8, wherein the work tool is a bucket.

15. A non-transitory computer usable storage medium having computer readable program code thereon for determining payload material density, comprising:
computer readable program code for identifying a capacity volume of a work tool;
computer readable program code for receiving a signal indicating that the work tool is loaded with an initial amount of loaded material matching the capacity volume;
computer readable program code for executing an onboard payload mass calculation algorithm to determine a mass of the initial amount of loaded material responsive to the signal;
computer readable program code for calculating a density of the initial amount of loaded material responsive to the mass of the initial amount of loaded material and the capacity volume;
computer readable program code for storing the density of the initial amount of loaded material; and
computer readable program code for calculating a productivity datum responsive to the density of the initial amount of loaded material and a subsequent amount of loaded material.

16. The non-transitory computer usable storage medium of claim 15, further including computer readable program code for receiving the capacity volume as an input from an operator interface.

17. The non-transitory computer usable storage medium of claim 15, further including computer readable program code for selecting the capacity volume from a work tool volume map stored in a memory.

18. The non-transitory computer usable storage medium of claim 15, further including:
computer readable program code for receiving a second signal indicating that the work tool is loaded with a subsequent amount of loaded material;
computer readable program code for executing the onboard payload mass calculation algorithm to determine a mass of the subsequent amount of loaded material responsive to the second signal; and
computer readable program code for calculating a volume of the subsequent amount of loaded material responsive to the mass of the subsequent amount of loaded material and the density of the initial amount of loaded material.

19. The non-transitory computer usable storage medium of claim 18, further including computer readable program code for calculating a fill factor value of the subsequent amount of loaded material responsive to the volume of the subsequent amount of loaded material and the capacity volume.

20. The non-transitory computer usable storage medium of claim 15, further including computer readable program code for transmitting a third signal corresponding to the productivity datum to an operator display.

* * * * *